(12) United States Patent
McCormick

(10) Patent No.: US 7,771,992 B2
(45) Date of Patent: Aug. 10, 2010

(54) APPARATUS AND METHOD FOR PREPARING TISSUE SAMPLES FOR HISTOLOGICAL EXAMINATION

(75) Inventor: James B. McCormick, Lincolnwood, IL (US)

(73) Assignee: Leica Biosystems Richmond, Inc., Richmond, IL (US)

( * ) Notice: Subject to any disclaimer, the term of this patent is extended or adjusted under 35 U.S.C. 154(b) by 2017 days.

(21) Appl. No.: 10/720,330

(22) Filed: Nov. 24, 2003

(65) Prior Publication Data

US 2005/0112031 A1 May 26, 2005

(51) Int. Cl.
*C12M 1/00* (2006.01)
*C12M 3/00* (2006.01)
*C12M 1/22* (2006.01)
*B65D 6/28* (2006.01)

(52) U.S. Cl. .............. 435/307.1; 435/305.4; 435/305.1; 435/305.2; 435/305.3; 211/126.2; 220/4.26; 220/4.27

(58) Field of Classification Search .............. 435/305.4, 435/305.1, 305.2, 305.3, 307.1; 211/126.2; 220/4.27; 200/4.26
See application file for complete search history.

(56) References Cited

U.S. PATENT DOCUMENTS

| | | | |
|---|---|---|---|
| 3,499,825 A * | 3/1970 | Falcone, Jr. et al. ...... | 435/305.1 |
| 4,440,301 A * | 4/1984 | Intengan ...................... | 206/456 |
| 5,035,326 A * | 7/1991 | Stahl .......................... | 206/507 |
| 5,080,869 A | 1/1992 | McCormick | |
| 5,240,854 A * | 8/1993 | Berry et al. .............. | 435/305.1 |
| 5,665,398 A | 9/1997 | McCormick | |
| 5,856,176 A * | 1/1999 | Mathus et al. ........... | 435/288.3 |
| 5,928,934 A | 7/1999 | McCormick | |
| 6,446,807 B1 * | 9/2002 | Lafond et al. ............... | 206/456 |
| 2003/0015132 A1 * | 1/2003 | Carter ......................... | 117/68 |

* cited by examiner

Primary Examiner—William H Beisner
Assistant Examiner—Nathan A Bowers
(74) Attorney, Agent, or Firm—Thompson Coburn LLP; Kevin M. Kercher, Esq.

(57) ABSTRACT

The present invention is directed to an assembleable unit of cassettes for containing specimens for histological examination. The cassettes are each designed for stacking relation one to another by snap locking means which are preferably configured to provide an audible sound and "click" feeling when stacked. A cover is provided to complete a stack, thereby providing an integral unit for case management. The unit is so integrated that it can be handled and will not disengage the stacked cassettes in the usual handling process in the laboratory. It is also readily processed in a paraffin bath for preparing the contained specimens for microtomy. Thus, a stabilized unit is provided for multiple specimens from a single source and maintaining them in sequential order without individual handling.

9 Claims, 3 Drawing Sheets

US 7,771,992 B2

APPARATUS AND METHOD FOR PREPARING TISSUE SAMPLES FOR HISTOLOGICAL EXAMINATION

FIELD OF THE INVENTION

The present invention relates generally to the preparation of tissue samples for histological examination, and more particularly relates to improved methods and apparatus for treatment of tissue samples in stabilized stacked cassettes prior to embedding the tissue samples in paraffin or the like in preparation for microscopic examination.

BACKGROUND OF THE INVENTION

Standard procedures for preparing tissue samples for microscopic examination involve embedding the tissue samples in paraffin and slicing paraffin-embedded tissues samples very thinly with a microtome. Examples to carry out this technique in plastic cassettes are described in my U.S. Pat. Nos. 5,080,869, 5,665,398, and 5,928,934, which are incorporated herein by reference. The '869 patent describes practicing the technique by way of stacked cassettes held in stacked array by means of a mechanical device. However, the stacked cassettes are not in a stabilized or self-sustaining stack for handling.

In the preparatory phase of histological tissue processing of biological tissues there are frequently multiple sections or specimens processed for the same case study. Research laboratories in Animal Biology and Biotechnology are frequently required to study multiple tissue samples from the same source. In the instance of human pathology studies there are about 50 percent of the cases that require multiples, as for example in autopsy tissue studies there are frequently 20 to 50 tissue samples that each require a processing cassette and in large specimen tumor studies such as lung or colon resections for cancer treatment six to ten samples are required. When multiple samples are prepared from the same surgical specimen, autopsy or animal study, it is desirable for processing efficiency to keep the samples together in numbered sequence and handleable as a group throughout preparation for microtome sectioning. I call this grouping "case management". Case management would be facilitated if a group of cassettes could be handled as a stabilized unit without handling individual cassettes during processing and if sensory signals of feeling and sound, or the "click" of audible assurance could be provided upon locking cassettes together.

It is a principle object of the invention to provide stackable cassettes which lock together to provide a stabilized stack of cassettes which can be handled as a unit.

It is another object of the invention to provide stackable cassettes which lock together with an audible sound and a sensory "click" feeling to assure adequate connection to the user.

It is a still further object of the invention to provide an improved method for case management.

SUMMARY OF THE INVENTION

The present invention is directed to an assembleable unit of cassettes for containing specimens for histological examination. The cassettes are each designed for stacking relation one to another by snap locking means which are preferably configured to provide an audible sound and "click" feeling when stacked. A cover is provided to complete a stack, thereby providing an integral unit for case management. The unit is so integrated that it can be handled and will not disengage the stacked cassettes in the usual handling process in the laboratory. It is also readily processed through the usual methods of dehydration, clearing, and infiltration with 53°-56° molten paraffin for preparing the contained specimens for microtomy. Thus, a stabilized unit is provided for multiple specimens from a single source and maintaining them in sequential order without individual handling.

Preferably, the stackable cassette for use in the preparation of specimens for histological examination comprises an open top container having two side walls, a front wall, a back wall, and a bottom wall, at least one side wall having a flexible leaf disposed therein. The cassettes also have a boss located below and inwardly of said flexible leaf.

The present invention is also directed to a system of stackable tissue processing cassettes comprising a plurality of superimposed stackable cassettes as described above. When stacked, the flexible leafs on an underlying cassette engage the bosses on an overlying cassette in a locking engagement. The locking engagement provides a sensory effect. The bottom wall of an overlying cassette provides a cover wall for an underlying cassette. In addition, the uppermost stacked cassette may engage a locking cover. The cover may also provide an identification surface.

Other objects and advantages of the invention will become apparent from the following description and reference to the accompanying drawings.

DETAILED DESCRIPTION OF THE PREFERRED EMBODIMENT

Figure 1:
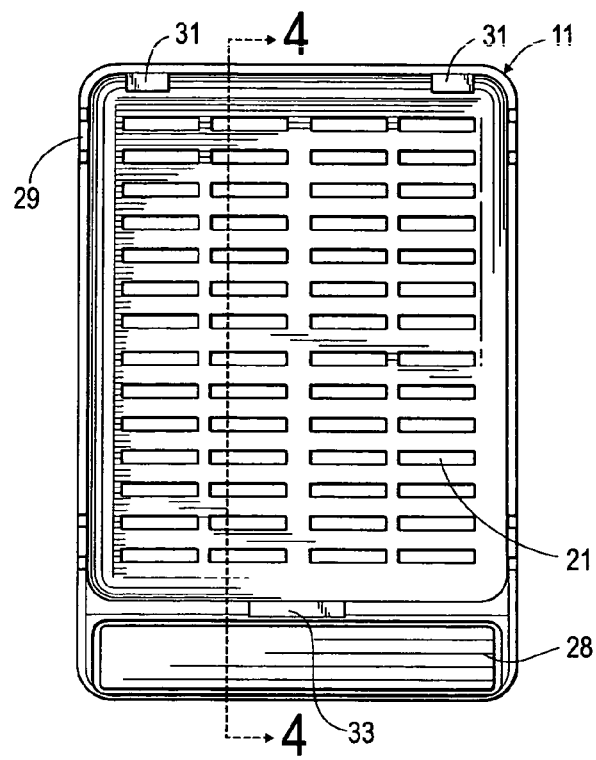
FIG. 1 is a top view of an exemplary stackable cassette in accord with the objects of the invention.
Figure 2:
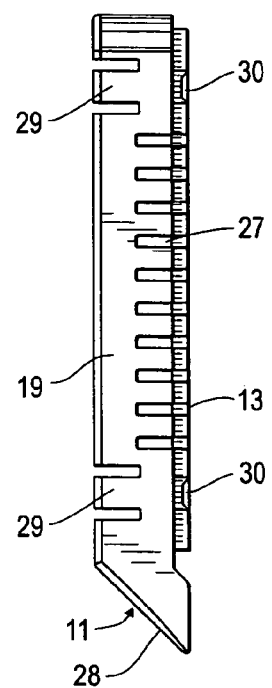
FIG. 2 is a side view of the cassette shown in FIG. 1.
Figure 3:
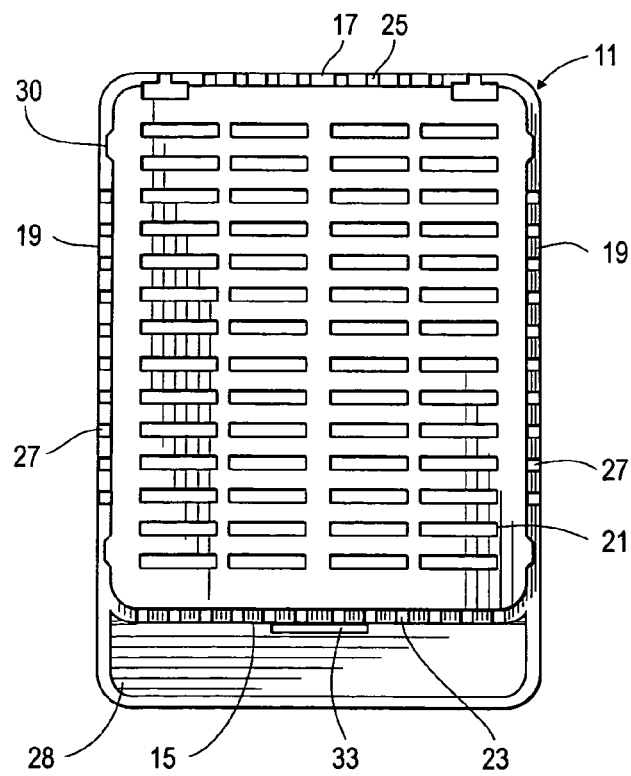
FIG. 3 is a bottom view of the cassette shown in FIG. 1.
Figure 4:
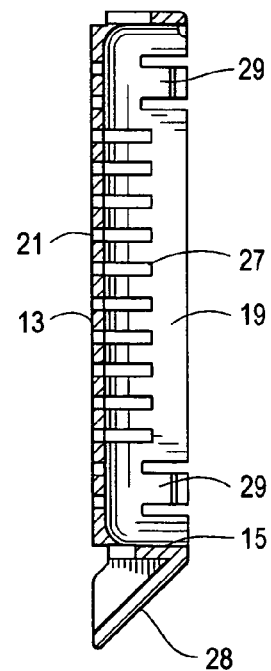
FIG. 4 is a view taken along lines 4 in FIG. 1.
Figure 5:
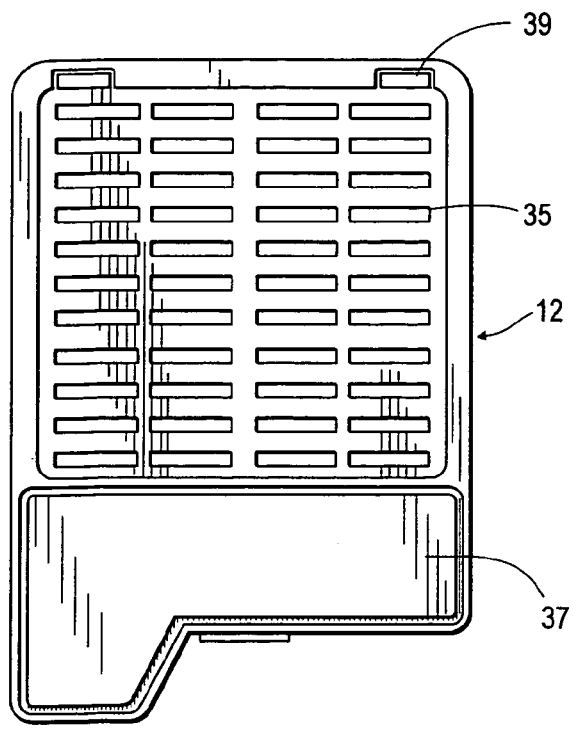
FIG. 5 is a top view of an exemplary cover for a stack of cassettes in accord with the objects of the invention.
Figure 6:
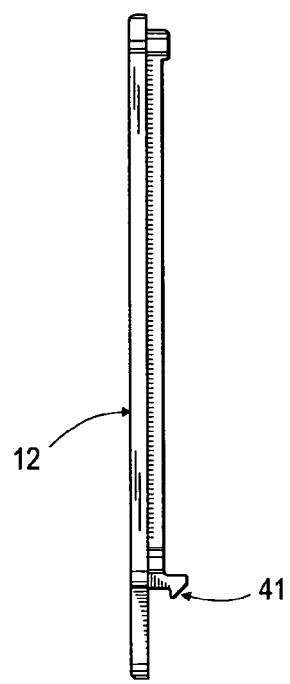
FIG. 6 is a side view of the cover shown in FIG. 5.
Figure 7:
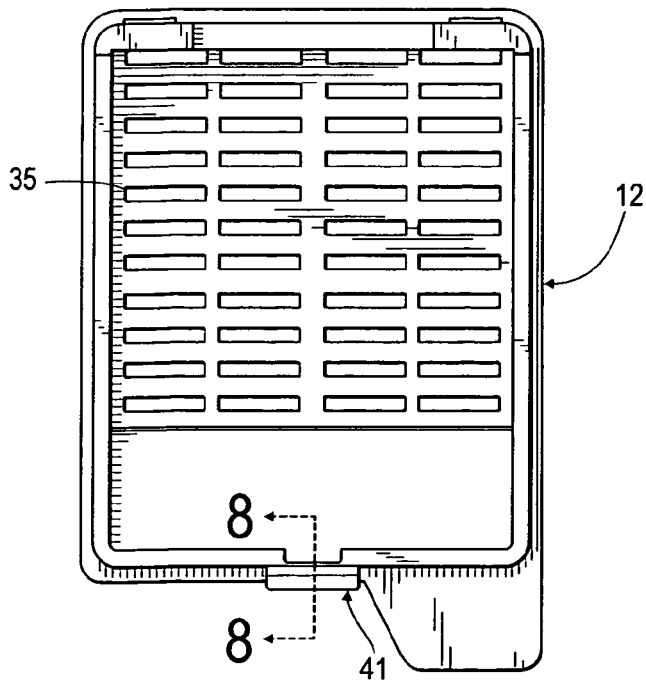
FIG. 7 is a bottom view of the cover shown in FIG. 5.

Generally illustrated in FIGS. 1-4 is a stacking cassette 11 of the invention. FIG. 1 is a top view, while FIG. 2 is a side view and FIG. 3 is a bottom view. FIG. 4 illustrates details of the earlier figures. FIGS. 5-8 generally illustrate a cover 12 for a stack of cassettes. FIG. 9 shows a stack of cassettes of the invention with cover.

Referring to FIGS. 1-4, there is illustrated a cassette 11 with an open top container adapted to contain a specimen for processing as described in U.S. Pat. No. 5,080,869, which is incorporated herein by reference. Cassette 11 comprises bottom wall 13, front wall 15, back wall 17, and two side walls 19. At least two opposing walls are provided with a plurality of apertures for passage of fluid through the cassette in a direction parallel to the plane of bottom wall 13 of cassette 11. When multiple cassettes 11 are stacked (FIG. 9), apertures in bottom walls 13 provide a continuous passageway for fluid which is orthogonal to bottom walls 13. The apertures in bottom wall 13 are numbered 21, while those in front wall 15 and back wall 17 are numbered 23 and 25, respectively. Apertures 27 are shown in side walls 19. Downwardly and forwardly extending from the upper edge of front wall 15 is facing plate 28 adapted for marking identification information.

Referring to FIGS. 2 and 4, each side wall 19 is provided with a pair of longitudinally spaced receiver leafs 29 which are adapted to snap lock onto a superimposed cassette 11. Below and inwardly of leafs 29 are bosses 30 for locking onto leafs 29 on an underlying cassette 11. Receiver leafs 29 are flexible so as to snap onto bosses 30 and preferably provide an audible sound and "click" feeling so that the user can be assured of locking engagement between cassettes 11. The locking engagement must have sufficient strength so that stacking of the cassettes is stabilized against breaking apart in usual handling in the laboratory and during processing of samples in cassettes 11.

Leafs 29, when engaging with bosses 30, preferably provide a sensory effect of sound and touch or a "click" feel that gives a signal of completion of engagement. It is further important that the engagement between leafs 29 and bosses 30 provide a locking engagement to withstand breaking apart under expected laboratory conditions of processing and occasional dropping. When engaged together, cassettes 11 are superimposed as shown in FIG. 9 and the topmost cassette 11 is provided with cover 12. It being understood that overlying cassettes serve as covers for cassettes stacked underneath them; as a result, when cassettes are stacked as in FIG. 9, only the topmost cassette 11 requires a cover.

Again referring to FIG. 1, cassette 11 is provided with a pair of inwardly extending cleats 31 in back wall 17 for locking engagement with cover 12. In addition, a cover lock receiver 33 is provided at front wall 15.

Figure 8:
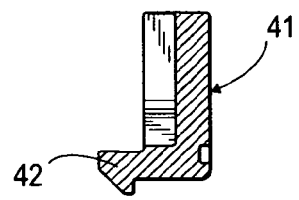
FIG. 8 is a view taken along lines 8 of FIG. 7.
Figure 9:
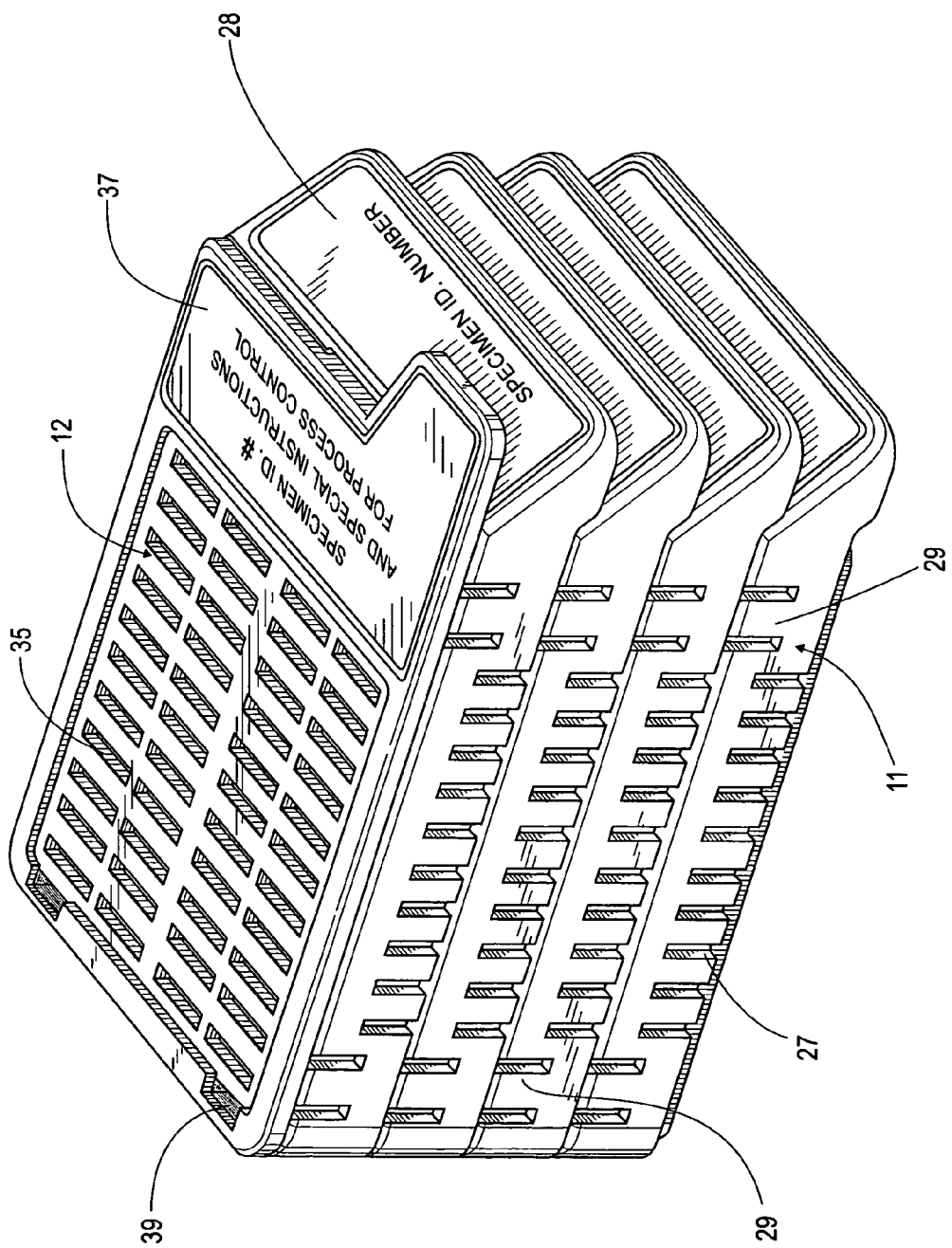
FIG. 9 shows an exemplary stack of cassettes and cover in accord with the objects of the present invention.

Referring to FIGS. 5-8, cover 12 is provided with vents 35 to permit flow of fluids during processing. At the forward end of cover 12 is a forwardly extending surface 37 that provides a writing surface for identification purposes. At the rear end of cover 12 are provided lock fingers 39 positioned for insertion and locking under receiving cleats 31 in an underlying cassette 11. At the forward end of cover 12 is a downwardly extending snap lock tab 41 for engaging receiver 33 in an underlying cassette 11. FIG. 8 shows a detailed view of downwardly extending snap lock tab 41. Tab 41 is substantially L-shaped with the foot of the L-shape terminating in an enlarged end 42. End 42 is angled upwardly and away from cover 12. Preferably, snap lock tab 41 will be flexible to provide an audible sound and "click" feel to assure locking of the cover in place. Of course, cover 12 should be coextensive with the cassette 11 and, when in place, provides for fluid flow through the stacked cassettes.

In practice, cassettes 11 are stacked after specimens are placed in them as described in my U.S. Pat. No. 5,080,869, which is incorporated herein by reference. Cover 12 is then snapped onto the topmost cassette 11. The stacking and covering are done with the sensory effects giving the assembler assurance of locking engagement. The stack can be handled and the specimens in the stack processed in usual ways, as for example, described in my U.S. Pat. No. 5,080,869, again, incorporated herein by reference. The described system provides improved case management with more efficiency and reduction of processing costs. Further, the identification surfaces provide for improved quality control for tissue processing.

It will be understood that various changes in the details, materials, and arrangements of parts and components which have been herein described and illustrated in order to explain the nature of the invention may be made by those skilled in the art within the principle and scope of the invention as expressed in the following claims.

What is claimed is:

1. A system of stackable tissue processing cassettes comprising:

a first cassette, the first cassette comprising a bottom wall, a front wall, a back wall, and two side walls with the bottom wall, the front wall, the back wall, and the side wall forming a first container having a top opening, wherein a histological specimen can be placed within the first container through the top opening of the first container; and a second cassette, the second cassette comprising a bottom wall, a front wall, a back wall, and two side walls with the bottom wall, the front wall, the back wall, and the side wall of the second cassette forming a second container, the bottom wall of the second cassette includes a plurality of apertures extending therethrough, wherein the first cassette can be interlocked with the second cassette such that the bottom wall of the second cassette closes the top opening of the first container to prevent the histological specimen from exiting the first container, wherein the plurality of apertures of the bottom wall of the second cassette allow liquid paraffin to flow from one of the first and second containers and into the other of the first and second containers while the first and second cassettes remain interlocked.

2. The system of stackable tissue processing cassettes in accordance with claim 1, wherein the second cassette can be interlocked with the first cassette when the second cassette is positioned relative to the first cassette and the first cassette and the second cassette are snapped together.

3. The system of stackable tissue processing cassettes in accordance with claim 2, wherein the first cassette interlocks with the second cassette such that when the first cassette is snapped together with the second cassette, there is a audible sound upon completion.

4. The system of stackable tissue processing cassettes in accordance with claim 3, wherein the bottom wall of the first cassette includes a portion having a generally planer upper face so that when the first cassette interlocks with the second cassette, the second cassette is moved relative to the first cassette in a direction generally perpendicular to the generally planer upper face so that the first cassette and the second cassette are snapped together.

5. The system of stackable tissue processing cassettes in accordance with claim 1, wherein the bottom wall of the first cassette includes a plurality of apertures extending therethrough.

6. The system of stackable tissue processing cassettes in accordance with claim 5, wherein each of the side walls of the first cassette includes a plurality of apertures extending therethrough.

7. The system of stackable tissue processing cassettes in accordance with claim 1, wherein the first cassette and the second cassette have generally identical geometry and dimensions.

8. A system of stackable tissue processing cassettes comprising:

a first cassette, the first cassette comprising a bottom wall, a front wall, a back wall, and two side walls with the bottom wall, the front wall, the back wall, and the side wall forming a first container having a top opening, wherein a histological specimen can be placed within the first container through the top opening of the first container; and a second cassette, the second cassette comprising a bottom wall, a front wall, a back wall, and two side walls, with the bottom wall, the front wall, the back wall, and the side wall forming a second container, the bottom wall of the second cassette comprising a plurality of apertures extending therethrough, wherein the first cassette can be interlocked with the second cassette, wherein the plurality of apertures of the bottom wall of the second cassette allow liquid paraffin to flow from one of the first and second containers and into the other of the first and second containers while the first and second cassettes remain interlocked.

9. The system of stackable tissue processing cassettes in accordance with claim 8, wherein the first cassette is devoid of a lid for closing the top opening of the first container, and the first cassette interlocks with the second cassette such that the bottom wall of the second cassette closes the top opening of the first container to prevent the histological specimen from exiting the first container.

\* \* \* \* \*